United States Patent
Messenger

(10) Patent No.: US 10,683,219 B2
(45) Date of Patent: Jun. 16, 2020

(54) DIVALENT ION REMOVAL FROM MONOETHYLENE GLYCOL-WATER STREAMS

(71) Applicant: Cameron Solutions, Inc., Houston, TX (US)

(72) Inventor: Brian E. Messenger, Hook (GB)

(73) Assignee: CAMERON SOLUTIONS, INC., Houston, TX (US)

( * ) Notice: Subject to any disclaimer, the term of this patent is extended or adjusted under 35 U.S.C. 154(b) by 590 days.

(21) Appl. No.: 14/247,003

(22) Filed: Apr. 7, 2014

(65) Prior Publication Data

US 2015/0284272 A1 Oct. 8, 2015

(51) Int. Cl.
| | |
|---|---|
| C02F 1/52 | (2006.01) |
| C02F 101/10 | (2006.01) |
| C07C 29/76 | (2006.01) |
| C10L 3/10 | (2006.01) |
| B01D 9/00 | (2006.01) |
| C02F 103/10 | (2006.01) |

(52) U.S. Cl.
CPC .......... *C02F 1/5245* (2013.01); *B01D 9/0054* (2013.01); *C07C 29/76* (2013.01); *C10L 3/107* (2013.01); *C02F 2101/10* (2013.01); *C02F 2101/101* (2013.01); *C02F 2103/10* (2013.01)

(58) Field of Classification Search
CPC ............... C02F 1/5245; C02F 2101/10; C02F 2101/101; C02F 2103/10; B01D 9/0054; C07C 29/76
See application file for complete search history.

(56) References Cited

U.S. PATENT DOCUMENTS

| | | | |
|---|---|---|---|
| 8,652,304 B2* | 2/2014 | Nazzer | B01D 1/18 159/2.1 |
| 9,085,477 B2* | 7/2015 | Banerjee | C02F 1/5245 |
| 2010/0191023 A1* | 7/2010 | Chen | C07C 29/88 568/920 |
| 2010/0319923 A1* | 12/2010 | Slabaugh | C02F 9/00 166/308.1 |
| 2012/0171554 A1 | 7/2012 | Kim | |
| 2013/0118989 A1* | 5/2013 | Caires Fernandez | C07C 29/76 210/723 |

(Continued)

FOREIGN PATENT DOCUMENTS

| | | |
|---|---|---|
| WO | 2009017971 A1 | 2/2009 |
| WO | 2012171554 A1 | 12/2012 |

(Continued)

*Primary Examiner* — Dirk R Bass
*Assistant Examiner* — Donovan Bui-Huynh
(74) *Attorney, Agent, or Firm* — Ronald G. Embry, Jr.

(57) ABSTRACT

A system and process for the removal of divalent ions from a MEG-water stream are presented. The system includes a chemical treatment tank that receives the MEG-water stream, means for precipitating the calcium, magnesium, and hydroxide ions that are contained in the MEG-water stream, means for discharging the MEG-water stream from the chemical treatment tank, and means for recycling the discharged MEG-water stream back to the chemical treatment tank or routing it to a solids removal system. The means for precipitating the calcium, magnesium, and sulfate ions may be employed simultaneously or sequentially.

5 Claims, 7 Drawing Sheets

(56) References Cited

U.S. PATENT DOCUMENTS

| | | | |
|---|---|---|---|
| 2014/0058140 A1* | 2/2014 | Phelps | B01D 15/00 568/917 |
| 2014/0066668 A1* | 3/2014 | Lorenz, II | C07C 29/76 568/913 |
| 2014/0235900 A1* | 8/2014 | Kaasa | C07C 29/76 568/868 |
| 2015/0083669 A1* | 3/2015 | Matherly | C02F 1/5236 210/723 |
| 2015/0112102 A1* | 4/2015 | Jensen | C09K 8/52 568/868 |
| 2015/0284272 A1* | 10/2015 | Messenger | C02F 1/5245 210/726 |

FOREIGN PATENT DOCUMENTS

| | | |
|---|---|---|
| WO | 2013179236 A1 | 12/2013 |
| WO | 2014035937 A3 | 3/2014 |

* cited by examiner

DIVALENT ION REMOVAL FROM MONOETHYLENE GLYCOL-WATER STREAMS

BACKGROUND

This invention relates to systems and processes designed to treat monoethylene glycol (MEG) used in the oil and gas industry, especially in offshore locations, to control the formation of hydrates. More particularly, the invention relates to systems and processes that are designed for the simultaneous removal of divalent cations and sulfate from MEG-water streams through the addition of alkalinity and barium ions.

In the oil and gas industry, MEG is widely used in wellheads and pipelines as a hydrate suppressor to prevent hydrate formation at pipeline conditions. On offshore gas production facilities, where the exposure to lower temperatures in subsea pipelines is significant, MEG is in prevalent use for hydrate inhibition. The lean (dry) MEG is injected in the subsea gas pipeline at or near the wellhead and mixes readily with the produced water. The inhibition process is straightforward, with the MEG decreasing the hydrate formation temperature below the operating temperature and thus preventing hydrate blockage of the pipeline.

After use, the MEG is recovered by removing the water and the dissolved salts, which are produced from the well along with the gas. The removal of water is conventionally referred to as MEG regeneration, while the removal of the dissolved salts is conventionally known as MEG reclamation. After regeneration and reclamation, the MEG can be re-used in hydrate control.

If the dissolved salts are not removed, they can form scale in pipelines and in processing equipment. The extent of scaling depends on the concentrations of the ions and process conditions such as temperature, pressure, and the concentration of carbon dioxide. As an example, as the MEG-water stream passes through MEG regeneration, the temperature is raised and scale may form from $Na_2SO_4$, $CaCO_3$ from unprecipitated calcium ions, and $Mg(OH)_2$ from unprecipitated magnesium ions. Scaling may reduce the efficiency of flow through the pipelines and cause the failure of downstream treatment processes.

Divalent cations can be removed by adding alkalinity in the form of carbonate ions, hydroxide ions, or both to raise the pH of the solution, which causes the divalent cations to precipitate as insoluble carbonates or hydroxides. However, raising the pH does not remove the sulfate ions. As a result, when the lean MEG is re-injected into the gas production pipeline and mixed with the produced water, the sulfate ions in the lean MEG and the calcium, magnesium, and sulfate ions in the produced water may combine to form scale in the pipeline.

A need exists for systems and processes for removing divalent ions from MEG-water streams in order to improve the efficiency of MEG reclamation and MEG regeneration and to prevent the accumulation of scale inside gas production pipelines and process equipment.

SUMMARY OF THE INVENTION

A system for the removal of divalent ions from a MEG-water stream is presented. The system includes a chemical treatment tank that receives the MEG-water stream, means for precipitating the calcium, magnesium, and sulfate ions that are contained in the MEG-water stream, means for discharging the MEG-water stream from the chemical treatment tank, and means for recycling the discharged MEG-water stream back to the chemical treatment tank or routing it to a solids removal system. The means for precipitating the calcium, magnesium, and sulfate ions may be employed simultaneously or sequentially.

A process for the removal of divalent ions from a MEG-water stream is also presented. The process includes the steps of routing a MEG-water stream containing calcium, magnesium, and sulfate ions to a chemical treatment tank, precipitating the sulfate ions in the MEG-water stream, precipitating the calcium ions in the MEG-water stream, precipitating the magnesium ions in the MEG-water stream, and discharging the MEG-water stream from the chemical treatment tank. If the precipitation steps occur simultaneously, the MEG-water stream is recycled to the chemical treatment tank until the precipitation reactions are complete and then routed to a solids removal system and filtrate tank for further processing. If the precipitation steps occur sequentially, the MEG-water stream is recycled to the chemical treatment tank until the precipitation reaction for barium sulfate is complete. The MEG-water stream is then routed to a solids removal system, where the barium sulfate is separated for disposal, and then recycled to the chemical treatment tank. The process is repeated for the step of precipitating the calcium ions and the magnesium ions.

The objects of this invention include (1) providing a more efficient process to remove divalent ions contained in a MEG-water stream; (2) providing for the quantitative removal of divalent ions and sulfate ions in the same treatment process; (3) minimizing the formation of scale in pipelines and downstream treatment processes; (4) reducing the need for the use of clean-in-place systems and scale inhibitors; and (5) reducing the amount of time the process equipment must be taken off-line for cleaning.

ELEMENTS AND NUMBERING USED IN THE DRAWINGS AND THE DETAILED DESCRIPTION

Figure 1:
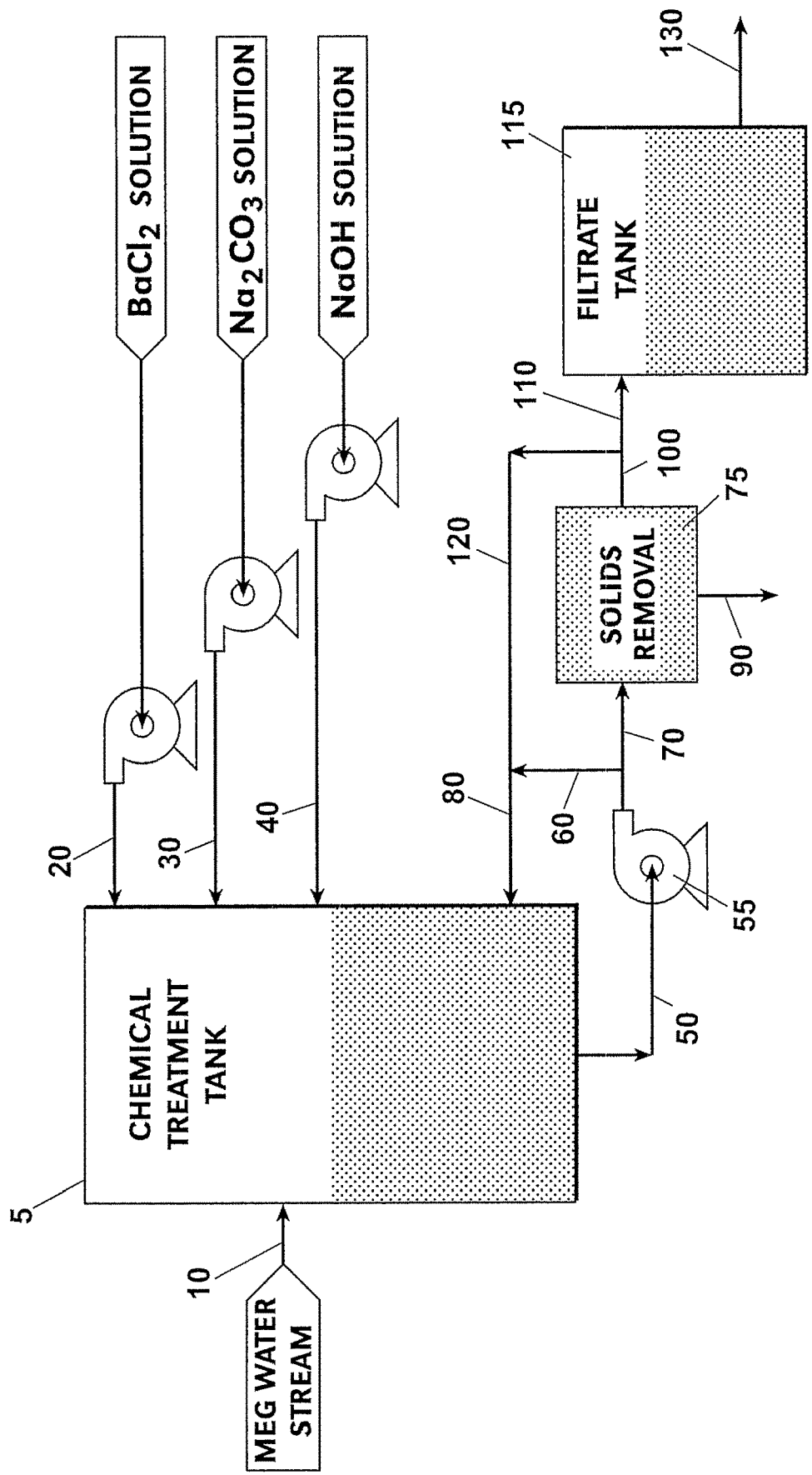
FIG. 1 is a preferred embodiment of a system and process practiced according to this invention.

5 Chemical treatment tank
10 MEG-water stream
20 Barium chloride injection line
30 Sodium carbonate injection line
40 Sodium hydroxide injection line
50 Exit line from chemical treatment tank
55 Mixing pump
60 Recycle line to chemical treatment tank
70 Line to solids removal system
75 Solids removal system
80 Recycle line to chemical treatment tank
90 Solids disposal
100 Filtrate/centrate from solids removal system
110 Filtrate/centrate to filtrate tank
115 Filtrate tank
120 Filtrate/centrate recycle line to chemical treatment tank
130 Exit line for MEG-water stream

DETAILED DESCRIPTION OF THE PREFERRED EMBODIMENTS

A system and process made and practiced according to this invention treats MEG-water streams so that the MEG can be re-used in the gas production pipeline system. More particularly, the system and process are designed for the simultaneous removal of divalent cations and sulfate from MEG-water streams through the addition of alkalinity and barium ions. Divalent cations may include, but are not limited to, calcium, magnesium, iron, strontium, and barium. Depending upon the concentration of divalent ions in the MEG-water stream, its pH, and other factors, the alkalinity may be a sodium carbonate solution, a sodium hydroxide solution, a potassium carbonate solution, a potassium hydroxide solution, or a combination of the above.

Referring to FIG. 1, a system for removing divalent ions from a MEG-water stream includes a chemical treatment tank 5 to receive the incoming MEG-water stream 10, which contains calcium, magnesium, and sulfate ions. The chemical treatment tank 5 also receives a barium chloride solution through a barium chloride injection line 20, a sodium carbonate solution through a sodium carbonate injection line 30, and a sodium hydroxide solution through a sodium hydroxide injection line 40. The weight percentage of barium chloride in the barium chloride solution may be approximately 20 percent at 25° C., the weight percentage of sodium carbonate in the sodium carbonate solution may be approximately 20 percent at 25° C., and the weight percentage of sodium hydroxide in the sodium hydroxide solution may be approximately 47 percent at 25° C. Potassium carbonate may be used as an alternative to sodium carbonate, and potassium hydroxide may be used as an alternative to sodium hydroxide.

After mixing, the MEG-water stream is carried away from the chemical treatment tank 5 by an exit line 50. The MEG-water stream may be pumped by a mixing pump 55 through recycle lines 60, 80 to the chemical treatment tank 5. Alternatively, the MEG-water stream may be pumped through line 70 to a solids removal system 75, where the precipitated solids are removed and sent for disposal 90. Solids removal systems such as filters and centrifuges are well-known in the art, and any suitable system may be used with the invention. The filtrate or centrate from the solids removal system 75 exits the system through line 100. From there, it may be recycled through line 120 to the chemical treatment tank 5 or sent through line 110 to the filtrate tank 115. The MEG-water stream from the filtrate tank 115 is then sent through exit line 130 to downstream equipment for additional treatment.

The precipitation of divalent ions and sulfate may occur simultaneously or sequentially. For simultaneous precipitation, the MEG-water stream 10 enters the chemical treatment tank 5. Barium chloride, sodium carbonate, and sodium hydroxide solutions are added to the chemical treatment tank 5 through lines 20, 30, and 40, respectively, at individual rates determined by the flow and characteristics of the MEG-water stream 10. The resulting mixture exits the chemical treatment tank 5 through line 50 and is recycled back to the tank 5 through lines 60 and 80 until the precipitation reactions are complete. The MEG-water stream 10 is then routed to the solids removal system 75 through line 70. The solids are sent for disposal 90, while the filtrate or centrate exits the solids removal system 75 through line 100. The filtrate or centrate is then routed to the filtrate tank 115 through line 110 and subsequently on to MEG regeneration.

For sequential precipitation, the MEG-water stream 10 enters the chemical treatment tank 5. A barium chloride solution is added to the chemical treatment tank 5 through line 20 at a rate determined by the flow and characteristics of the MEG-water stream. The resulting mixture exits the chemical treatment tank 5 through line 50 and is recycled back to the tank 5 through lines 60 and 80 until the precipitation reaction for barium sulfate is complete. The stream is then routed to the solids removal system 75 through line 70. The barium sulfate solids are sent for disposal 90, while the filtrate or centrate exits the solids removal system 75 through line 100 and is routed to the chemical treatment tank 5 through line 120. The process is repeated a second time for the addition of a sodium carbonate solution through line 30, which results in the precipitation of the calcium ions as calcium carbonate, and the addition of a sodium hydroxide solution through line 40, which results in the precipitation of the magnesium ions as magnesium hydroxide. Alternatively, the process is repeated a second time for the addition of a sodium carbonate solution through line 30, which results in the precipitation of the calcium ions as calcium carbonate, and a third time for the addition of a sodium hydroxide solution through line 40, which results in the precipitation of the magnesium ions as magnesium hydroxide. The individual rates of addition for the sodium carbonate and sodium hydroxide solutions are determined by the flow and characteristics of the MEG-water stream 10. After all the solids have been separated for disposal 90 by the solids removal system 75, the remaining filtrate or centrate is routed to the filtrate tank 115 through line 110 for further processing.

Experimental Results

Figure 2:
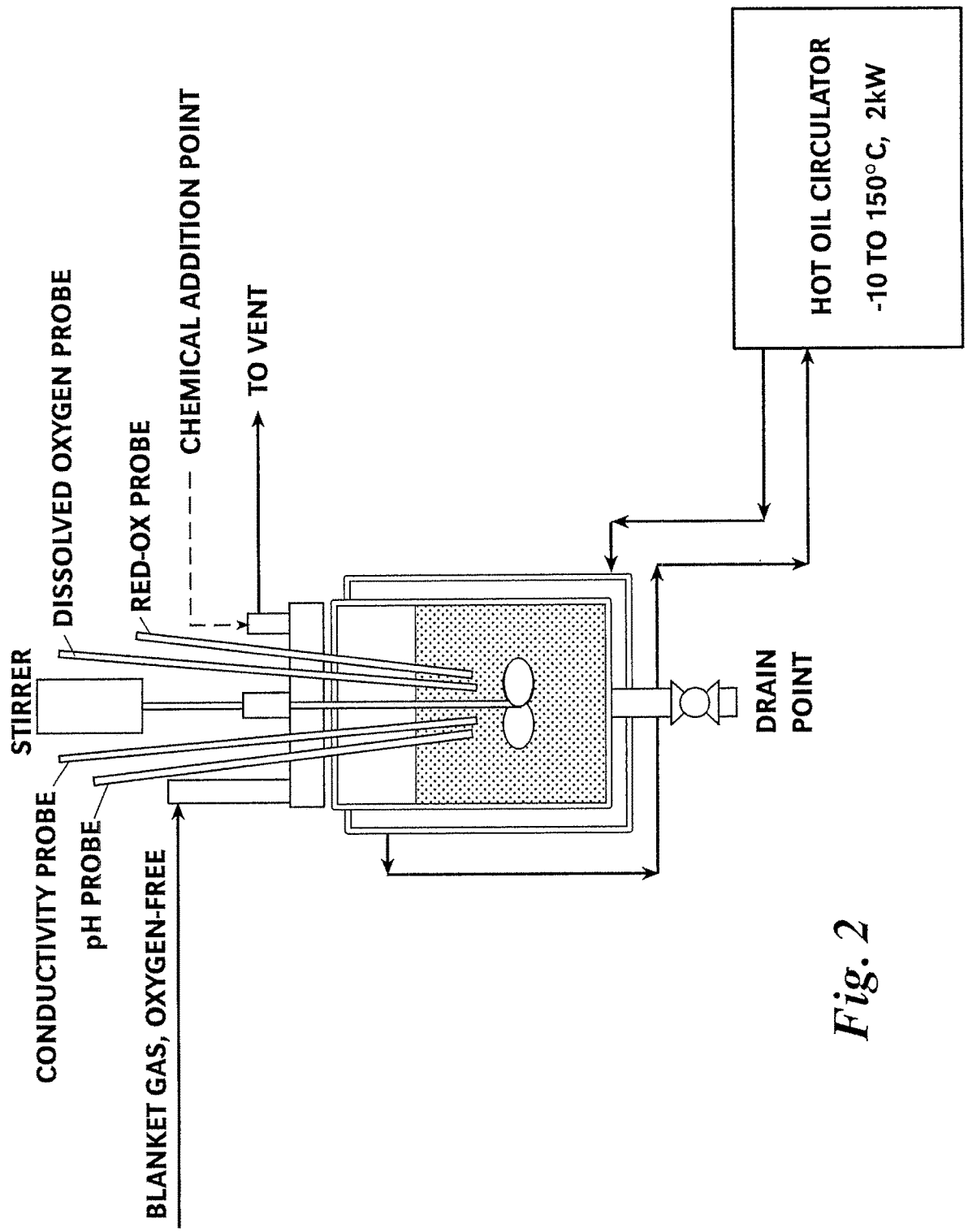
FIG. 2 is a schematic of an apparatus used to test preferred embodiments of the system and process of this invention.

The equipment used to test the simultaneous precipitation of magnesium, calcium, and sulfate ions is shown in FIG. 2. The equipment includes a double-skinned 5L glass reaction vessel with a stirrer. The reaction vessel is connected to a hot oil circulator bath which allows the temperature of the reaction vessel to be adjusted between −10° C. and 150° C. The reaction vessel is fitted with a pH probe (Hamilton Polilyte Plus ARC 425), dissolved oxygen probe (Hamilton Oxygold G ARC 425), electrical conductivity probe (Hamilton Conducell 4USF ARC PG425), RedOx probe (Hamilton Polilyte Plus ORP ARC 425), and a thermocouple (not shown) to measure liquid temperature during the progression of the test. A small flow of nitrogen (100 mL/min) was passed through the vapor space above the liquid inventory. Liquids were added to the reaction vessel through nozzles located at the top of the vessel. All samples were taken through a drain point at the base of the reaction vessel.

Sequential Addition of $BaCl_2$, $Na_2CO_3$ and NaOH

A first experimental test solution as shown in TABLE 1 was loaded into the reaction vessel.

TABLE 1

First Experimental Test Solution

|  | Water | MEG | NaCl | $MgCl_2$ | $CaCl_2$ | $Na_2SO_4$ | $NaHCO_3$ |
|---|---|---|---|---|---|---|---|
| grams | 1,593 | 2,349 | 129 | 1.83 | 17.33 | 2.93 | 1.74 |
| mmoles | — | — | 2,207 | 19.2 | 156.1 | 20.6 | 20.7 |

The test solution was heated to 30° C. when a first sample was taken for analyses (SAMPLE 1, approximately 30 grams). Dissolved cations ($Na^+$, $K^+$, $Mg^{2+}$, $Ca^{2+}$, $Fe^{2+}$, $Sr^{2+}$, $Ba^{2+}$) were measured using Inductively-Coupled Plasma Optical Emission Spectroscopy (ICP-OES). Dissolved anions ($Cl^-$, $Br^-$, $SO_4^{2-}$) were measured using Ion Chromatography (IC). The test solution was then heated to 61.5° C. and a second sample was taken (SAMPLE 2, approximately 30 grams). 20.79 grams of 20 wt % barium chloride solution (20 wt % $BaCl_2$ in water, equivalent to 4.158 grams of barium chloride, 20.0 mmoles) were then added to the reaction vessel. The resulting solution was allowed to mix for fifteen minutes and a third sample was taken (SAMPLE 3, approximately 30 grams).

90.93 grams of 20 wt % sodium carbonate solution (20 wt % $Na_2CO_3$ in water, equivalent to 18.19 grams of sodium carbonate, 171.6 mmoles) were added to the reaction vessel and a fourth sample was taken (SAMPLE 4). A further 10 grams of 20 wt % sodium carbonate solution were added to elevate the solution pH to 9.5 and a fifth sample was taken (SAMPLE 5). The total amount of sodium carbonate added to the first experimental test solution was 20.19 grams or 190.4 mmoles.

3.20 grams of 50 wt % sodium hydroxide solution (50 wt % NaOH in water, containing 1.6 g of sodium hydroxide, 40 mmoles) were added to the reaction vessel, which elevated the pH of the first experimental test solution to 10.0, and a sixth sample was taken (SAMPLE 6). Finally, an additional 8.56 grams of 50 wt % sodium hydroxide solution were added to the reaction vessel to elevate the pH to 10.59 and a seventh sample was taken (SAMPLE 7). The total amount of sodium hydroxide added to the first experimental test solution was 5.88 grams or 147.0 mmoles.

Figure 3:
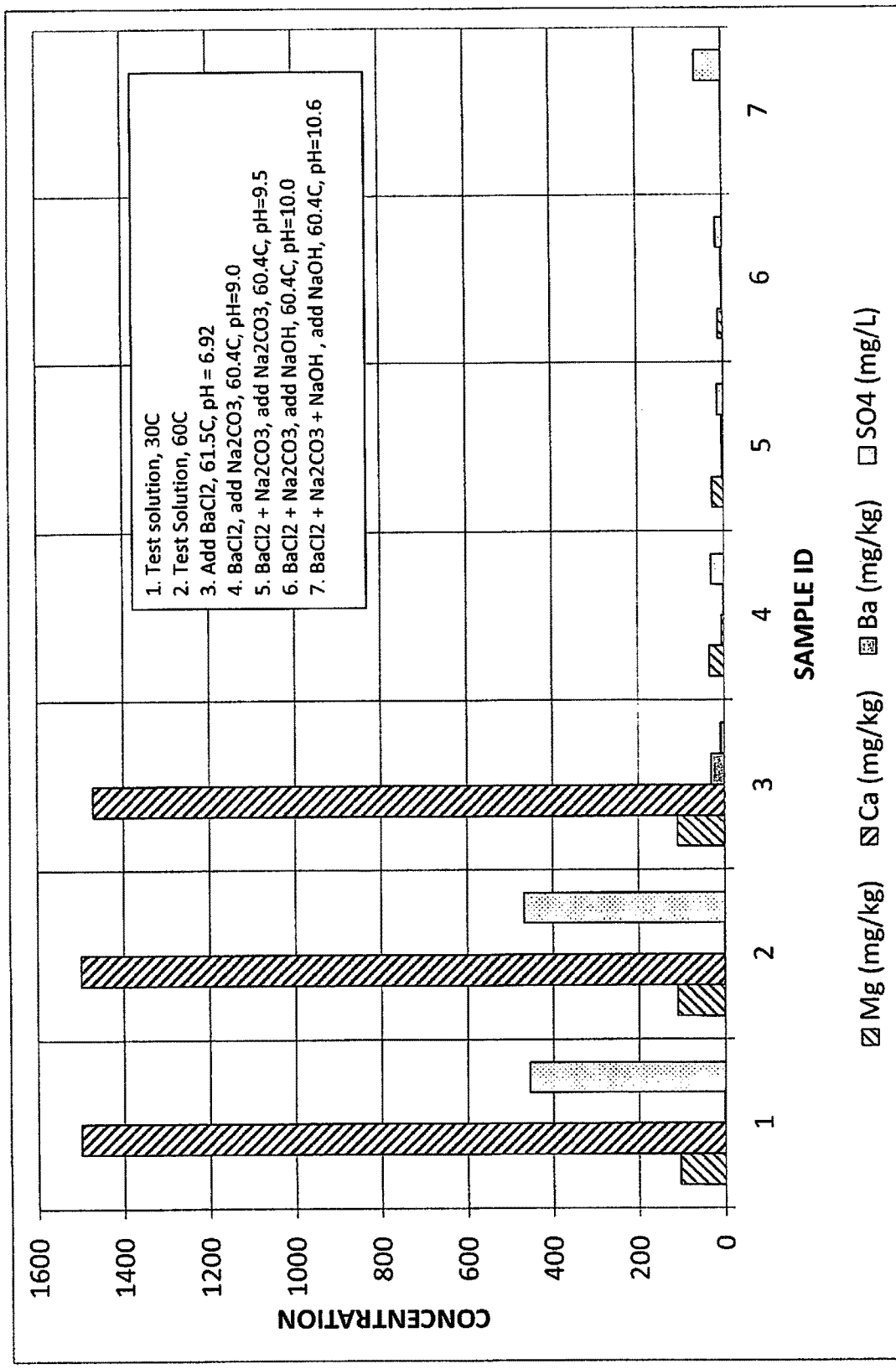
FIG. 3 shows experimental results of a system and process made according to FIG. 1 for the removal of magnesium, calcium, barium, and sulfate ions from a first experimental test solution.

Analytical results for SAMPLES 1-7 are shown in FIG. 3 and TABLE 2.

TABLE 2

Analytical Results

| | | SAMPLE # | | | | | | |
|---|---|---|---|---|---|---|---|---|
| | — | 1 | 2 | 3 | 4 | 5 | 6 | 7 |
| $BaCl_2$ AQ (20%) | g | — | — | 20.8 | 20.8 | 20.8 | 20.8 | 20.8 |
| $Na_2CO_3$ AQ (20 wt %) | g | — | — | — | 90.9 | 100.2 | 100.2 | 100.2 |
| NaOH AQ (20 wt %) | g | — | — | — | — | — | 3.2 | 11.8 |
| TEMP | deg C. | 30 | 60 | 61.5 | 60.4 | 60.4 | 60.4 | 60.4 |
| pH | — | 6.97 | 7.28 | 6.91 | 8.99 | 9.54 | 10 | 10.59 |
| Na | mg/kg | 12,400 | 12,300 | 12,400 | 13,900 | 13,900 | 14,200 | 14,600 |
| K | mg/kg | <25 | <25 | <25 | <25 | <25 | <25 | <25 |
| Mg | mg/kg | 105 | 111 | 110 | 35 | 27 | 11 | 0.3 |
| Ca | mg/kg | 1500 | 1500 | 1470 | 6.4 | 3.1 | 2.5 | 0.1 |
| Fe | mg/kg | <0.7 | <0.7 | <0.7 | <0.7 | <0.7 | <0.7 | <0.7 |
| Sr | mg/kg | 0.63 | 0.63 | 0.4 | <0.04 | <0.04 | <0.04 | <0.04 |
| Ba | mg/kg | <0.1 | <0.1 | 31.7 | 0.43 | 4 | 3.2 | 0.22 |
| Zn | mg/kg | 0.65 | 0.49 | 0.6 | 0.51 | <0.4 | <0.4 | 0.6 |
| S | mg/kg | 162 | 165 | <18 | <18 | <18 | <18 | 19 |
| Cl | mg/L | 30,744 | 23,191 | 22,885 | 22,502 | 21,545 | 22,332 | 22,667 |
| Br | mg/L | 4.4 | 4.4 | 4.4 | 4.3 | 4.4 | 4.6 | 4.5 |
| $NO_3$ | mg/L | 3.1 | 3.1 | 3.2 | 3 | 3 | 2.9 | 2.9 |
| $PO_4$ | mg/L | 5.7 | 5.1 | 5.1 | 5.1 | 5.4 | 5.2 | 8.8 |
| $SO_4$ | mg/L | 454.9 | 467.1 | 10 | 30.9 | 14.9 | 15.4 | 61.5 |

Figure 4:
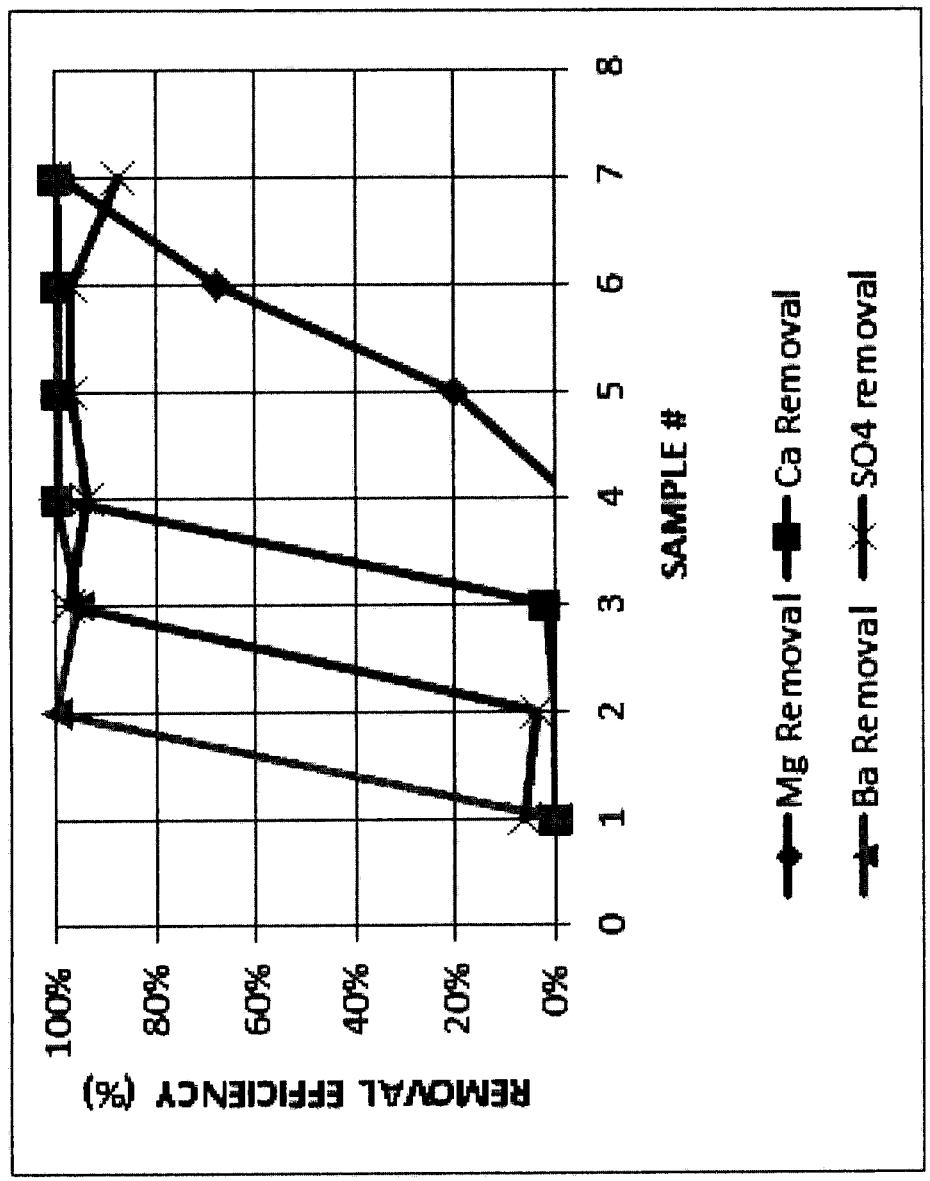
FIG. 4 shows experimental results of a system and process made according to FIG. 1 for the removal of magnesium, calcium, barium, and sulfate ions from a first experimental test solution, according to the removal efficiency in percent for each ion.

Removal efficiencies for magnesium, calcium, barium, and sulfate ions are shown in FIG. 4 and TABLE 3. The removal efficiency is calculated using the following formula:

$$\text{Removal Efficiency of Species } X = \frac{\text{Concentration of species } X \text{ in feed (ppm)} - \text{Concentration of species } X \text{ in sample (ppm)}}{\text{Concentration of species } X \text{ in feed (ppm)}}$$

$$X = Mg^{2+}, Ca^{2+}, SO_4^{2-}$$

For barium removal, the "concentration of species X in feed" was based on the quantity of barium chloride solution added to the test solution.

TABLE 3

| Calculated $M^{2+}$ and $SO_4^{2-}$ Removal Efficiencies | | | | | | | | |
|---|---|---|---|---|---|---|---|---|
| | | SAMPLE # | | | | | | |
| | — | 1 | 2 | 3 | 4 | 5 | 6 | 7 |
| $BaCl_2$ AQ (20%) | g | — | — | 20.8 | 20.8 | 20.8 | 20.8 | 20.8 |
| $Na_2CO_3$ AQ (20 wt %) | g | — | — | — | 90.9 | 100.2 | 100.2 | 100.2 |
| NaOH AQ (20 wt %) | g | — | — | — | — | — | 3.2 | 11.8 |
| TEMP | deg C. | 30 | 60 | 61.5 | 60.4 | 60.4 | 60.4 | 60.4 |
| pH | — | 6.97 | 7.28 | 6.91 | 8.99 | 9.54 | 10 | 10.59 |
| Mg | % PPTD | — | — | — | — | 20.1 | 67.5 | 99.1 |
| Ca | % PPTD | — | — | 1.5 | 99.6 | 99.8 | 99.8 | 100.0 |
| Ba | % PPTD | — | 100.0 | 99.4 | 99.9 | 99.4 | 99.5 | 100.0 |
| $SO_4$ | % PPTD | — | 3.6 | 97.9 | 93.6 | 96.9 | 96.8 | 87.3 |

As shown in TABLE 2 and FIG. 3, there was little precipitation from the first experimental test solution on original mixing (SAMPLE 1) and when the solution temperature was increased to 60° C. (SAMPLE 2). SAMPLE 3 shows that the addition of barium chloride (4.16 grams, 20.0 mmoles) resulted in almost quantitative removal of the sulfate anions in the test solution, with sulfate concentrations falling from 467 mg/L to 10 mg/L (97.9% removal). The measured barium concentration increased from <0.1 mg/kg to 32 mg/kg. This corresponds to removal of 95.3% of the barium added as barium chloride. However, calcium and magnesium levels before and after the addition of barium chloride were unchanged.

The addition of alkalinity (as sodium carbonate and sodium hydroxide) resulted in quantitative removal of the calcium. At a pH of 9.0 (SAMPLE 4), the measured calcium concentration decreased from 1,470 mg/kg to 6.4 mg/kg. Calcium concentrations continued to decrease as the pH increased. The final calcium concentration, measured at a pH of 10.6 (SAMPLE 7), was 0.1 mg/kg, which corresponds to 99.99% calcium removal. The barium present after the addition of barium chloride (31.7 mg/kg in SAMPLE 3) also precipitated as the pH increased. The final barium concentration (SAMPLE 7), was 0.22 mg/kg, which corresponds to 99.97% barium removal.

Because magnesium is more soluble in alkaline carbonate solutions than both calcium and barium, a higher pH is required to precipitate magnesium from the test solution. At a pH of 9.0 (SAMPLE 4), the measured magnesium concentration was 35 mg/kg, which corresponds to precipitation of 69% of the magnesium originally present in the solution. As the pH increased to 10.0, the magnesium concentration decreased to 11 mg/kg, which corresponds to 90.4% magnesium precipitation (SAMPLE 6). At a pH of 10.6, the magnesium concentration was 0.3 mg/kg, which corresponds to 99.7% magnesium removal (SAMPLE 7).

Figure 5:
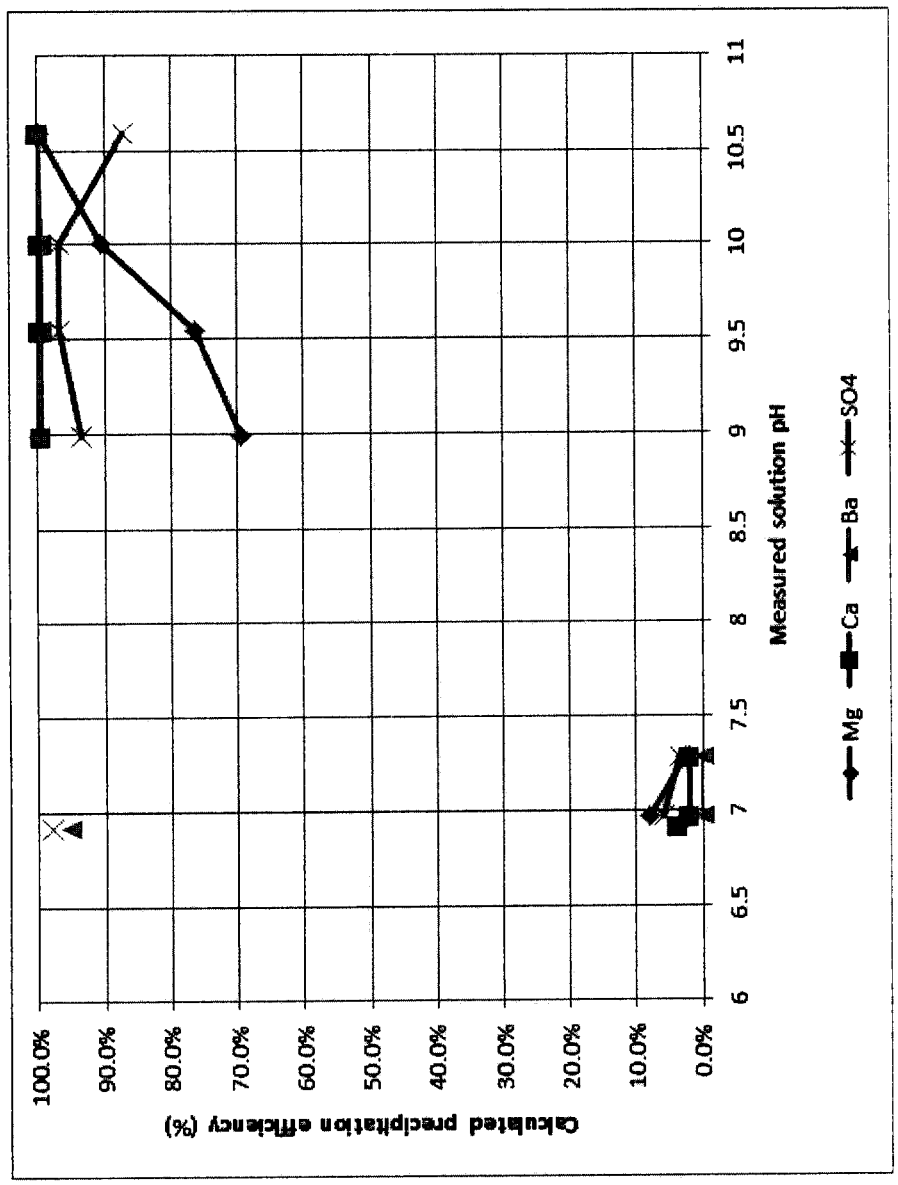
FIG. 5 shows experimental results of a system and process made according to FIG. 1 for the removal of magnesium, calcium, barium, and sulfate ions from a first experimental test solution. The calculated precipitation efficiency for each ion is plotted against the measured pH of the test solution.

It can be seen from TABLES 2 and 3 that sulfate precipitation occurs at low pH when barium chloride is added and that the sulfate remains in the solid phase at pH up to 10.0. However, some re-dissolution of the sulfate occurs at higher pH. As an example, measured sulfate levels varied from 15 mg/L to 31 mg/L over the pH range of 9.0 to 10.0, which corresponds to sulfate precipitation of 94% to 97%. At a pH of 10.6, the measured sulfate level was 60 mg/L, which corresponds to sulfate precipitation of only 87%. FIG. 5, which plots the precipitation of magnesium, calcium, barium, and sulfate ions against the pH of the test solution, further illustrates that the precipitation efficiency of sulfate decreases at higher pH. Effective pH monitoring and control is therefore required in order to optimize the precipitation of divalent cations and sulfate.

Simultaneous Addition of $BaCl_2$, $Na_2CO_3$ and NaOH

A second experimental test solution was prepared as per TABLE 4.

TABLE 4

| Second Experimental Test Solution | | | | | | |
|---|---|---|---|---|---|---|
| | Water | MEG | NaCl | $MgCl_2$ | $CaCl_2$ | $Na_2SO_4$ | $NaHCO_3$ |
| g | 1,648 | 2,542 | 127 | 0.56 | 17.47 | 3.03 | 0 |
| mmoles | — | — | 2,173 | 5.88 | 157.39 | 21.32 | 0 |

Solutions of barium chloride, sodium carbonate, and sodium hydroxide were prepared as per TABLES 5-7.

TABLE 5

| Barium Chloride Solution | | | | | |
|---|---|---|---|---|---|
| $BaCl_2 \cdot 2H_2O$ g | $BaCl_2 \cdot 2H_2O$ mmoles | WATER g | SOLUTION g | $BaCl_2$ wt % | $BaCl_2/$Ba g |
| 5.22 | 21.38 | 20.03 | 25.25 | 17.6 | 4.44/2.93 |

TABLE 6

| Sodium Carbonate Solution | | | | |
|---|---|---|---|---|
| $Na_2CO_3$ g | $Na_2CO_3$ mmoles | WATER g | SOLUTION g | $Na_2CO_3$ wt % |
| 20.02 | 188.87 | 95.99 | 116.01 | 17.3 |

TABLE 7

| Sodium Hydroxide Solution | | | | |
|---|---|---|---|---|
| NaOH g | NaOH mmoles | WATER g | SOLUTION g | NaOH wt % |
| 0.59 | 14.75 | 7.16 | 7.75 | 7.6 |

The second experimental test solution was heated at atmospheric pressure to 60° C. with continuous stirring. The barium chloride, sodium carbonate, and sodium hydroxide solutions were then added in 25% aliquots at 2.5-minute intervals and samples were taken as shown in TABLE 8 below.

TABLE 8

Chemical Addition

| ELAPSED TIME minutes | BaCl₂ soltn g | Na₂CO₃ soltn g | NaOH soltn G | Measured pH | SAMPLE ID |
|---|---|---|---|---|---|
| — | 0 | 0 | 0 | 7.85 | 1 |
| 2.5 | 6.31 | 29 | 1.9 | 8.85 → 8.70 | 2 |
| 5 | 12.63 | 58 | 3.9 | 9.04 → 9.00 | 3 |
| 7.5 | 18.94 | 87 | 5.8 | 9.26 → 9.24 | 4 |
| 10 | 25.25 | 116 | 7.8 | 9.70 | 5 |
| 15 | 25.25 | 116 | 7.8 | 9.70 | 6 |
| 20 | 25.25 | 116 | 7.8 | 9.70 | 7 |
| 30 | 25.25 | 116 | 7.8 | 9.70 | 8 |
| 60 | 25.25 | 116 | 7.8 | 9.70 | 9 |

Figure 6:
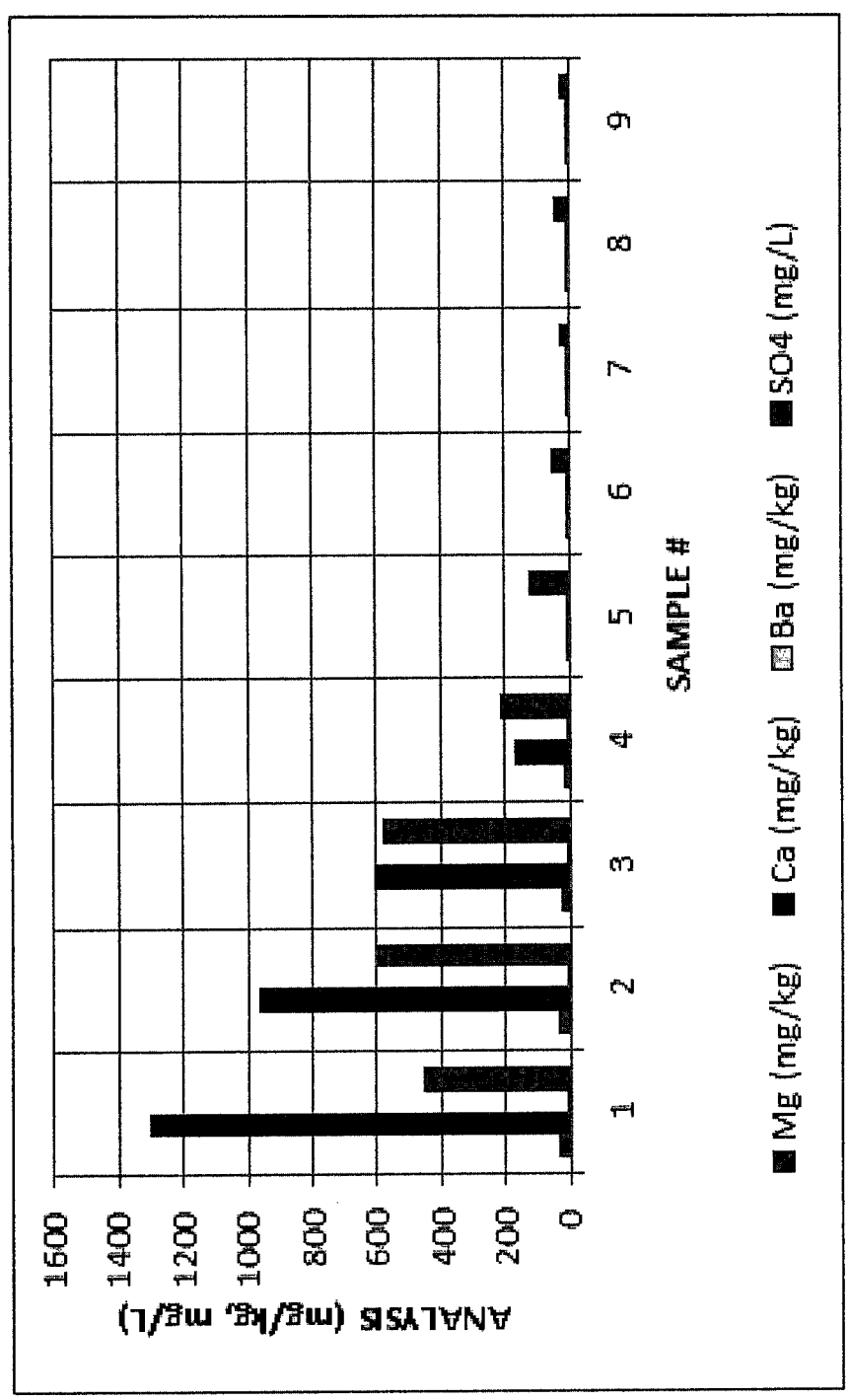
FIG. 6 shows experimental results of a system and process made according to FIG. 1 for the removal of magnesium, calcium, barium, and sulfate ions from a second experimental test solution.

The addition of the barium chloride, sodium carbonate, and sodium hydroxide solutions to the second experimental test solution shown in TABLE 4 results in a solution containing 653 ppm of barium. The analytical results for SAMPLES 1-9 are shown in TABLE 9 and illustrated in FIG. 6.

TABLE 9

Analytical Results

| | | SAMPLE # | | | | | | | |
|---|---|---|---|---|---|---|---|---|---|
| — | | 1 | 2 | 3 | 4 | 5 | 6 | 7 | 8 | 9 |
| Na | mg/kg | 11,400 | 11,600 | 12,500 | 12,600 | 12,800 | 13,000 | 13,100 | 13,000 | 13,300 |
| K | mg/kg | <30 | <30 | <30 | <30 | <30 | <30 | <30 | <30 | <30 |
| Mg | mg/kg | 33 | 31 | 26 | 14 | 0.6 | 1.2 | 1.7 | 1.3 | 1.2 |
| Ca | mg/kg | 1,300 | 964 | 601 | 168 | 2 | 3 | 2.9 | 2.6 | 22 |
| Fe | mg/kg | <0.7 | <0.7 | <0.7 | <0.7 | <0.7 | <0.7 | <0.7 | <0.7 | <0.7 |
| Sr | mg/kg | 0.58 | 0.3 | 0.14 | 0.06 | <0.05 | <0.05 | <0.05 | <0.05 | <0.05 |
| Ba | mg/kg | 0.3 | 0.1 | 0.1 | 0.2 | 0.3 | 0.6 | 1.7 | 0.8 | 1.5 |
| Zn | mg/kg | 0.6 | 0.6 | 0.8 | 0.9 | 1.2 | 0.6 | 0.7 | <0.5 | <0.5 |
| S | mg/kg | 164 | 186 | 187 | 65 | 39 | <20 | <20 | <20 | <20 |
| Cl | mg/L | 22,394 | 22,084 | 21,317 | 20,989 | 22,417 | 20,499 | 19,424 | 21,201 | 21,134 |
| Br | mg/L | 748 | 742 | 726 | 722 | 724 | 748 | 719 | 732 | 728 |
| NO₃ | mg/L | 372 | 433 | 266 | 324 | 268 | 240 | 186 | 338 | 163 |
| PO₄ | mg/L | 801 | 832 | 853 | 802 | 815 | 787 | 787 | 794 | 793 |
| SO₄ | mg/L | 449 | 592 | 578 | 214 | 122 | 53 | 24 | 41 | 25 |

Figure 7:
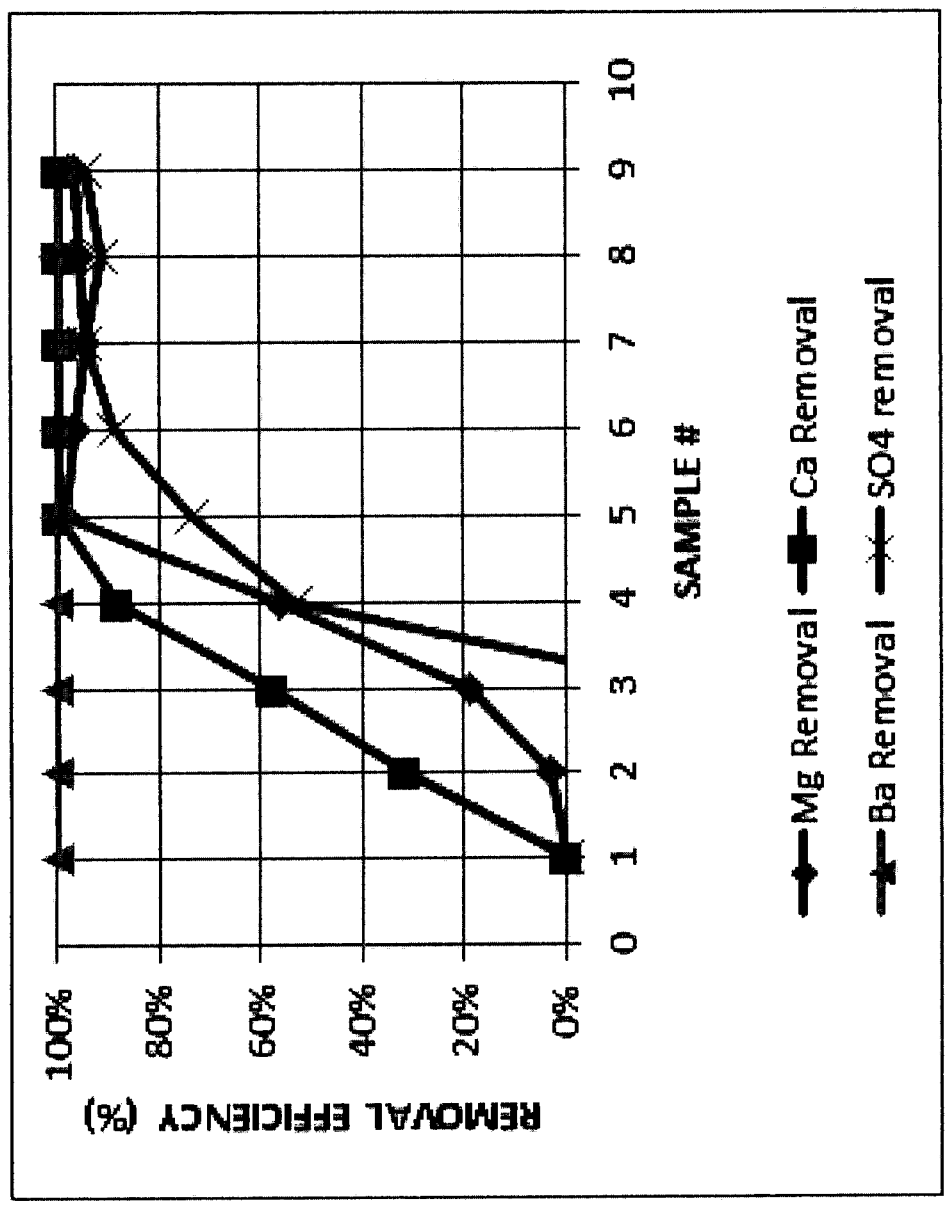
FIG. 7 shows experimental results of a system and process made according to FIG. 1 for the removal of magnesium, calcium, barium, and sulfate ions from a second experimental test solution, according to the removal efficiency in percent for each ion.

TABLE 10 and FIG. 7 show the calculated removal efficiencies for magnesium, calcium, and sulfate from the original solution as well as for the added barium.

TABLE 10

Precipitation Efficiency

| | | SAMPLE # | | | | | | | |
|---|---|---|---|---|---|---|---|---|---|
| — | | 1 | 2 | 3 | 4 | 5 | 6 | 7 | 8 | 9 |
| Mg | % precipitated | — | 3.1 | 18.8 | 56.3 | 98.1 | 96.3 | 94.7 | 95.9 | 96.3 |
| Ca | % precipitated | — | 31.8 | 57.5 | 88.1 | 99.9 | 99.8 | 99.8 | 99.8 | 99.8 |
| Ba[1] | % precipitated | — | 100.0 | 100.0 | 100.0 | 100.0 | 99.9 | 99.7 | 99.9 | 99.8 |
| SO₄ | % precipitated | — | — | — | 53.4 | 73.4 | 88.4 | 94.6 | 91.1 | 94.6 |

[1]The barium precipitated refers to the barium which was added to the test solution. The calcium and magnesium removal efficiencies refer to the calcium and magnesium originally present in the test solution.

As shown in the referenced tables and figures, the quantitative removal of sulfate, magnesium, and calcium ions can be achieved in twenty to twenty-five minutes at 60° C. by the addition of stoichiometric quantities of barium, hydroxide, and carbonate, respectively.

Simulated Results

Simulated results were obtained employing OLI Stream Analyzer™ software (OLI Systems, Inc., Cedar Knolls, N.J.). A solution without bicarbonate (First Model Test Solution, TABLE 11) was modeled for divalent cation and sulfate removal.

TABLE 11

First Model Test Solution

| | kg | mg/kg | mol | mmol/kg |
|---|---|---|---|---|
| Water | 1500 | — | — | — |
| Monoethylene glycol | 1500 | — | — | — |
| Sodium chloride | 100 | 32105 | 1710.9 | 549.3 |
| Magnesium chloride | 1.00 | 321 | 10.5 | 3.4 |
| Calcium chloride | 13.00 | 4174 | 117.1 | 37.6 |
| Sodium sulfate | 0.80 | 257 | 5.6 | 1.8 |
| Sodium bicarbonate | 0.00 | 0 | 0.0 | 0.0 |
| | 3114.8 | | | |

A second solution containing 770 mg/kg of sodium bicarbonate (Second Model Test Solution, TABLE 12) was also modeled for divalent cation and sulfate removal.

TABLE 12

Second Model Test Solution

| | kg | mg/kg | mol | mmol/kg |
|---|---|---|---|---|
| Water | 1500 | — | — | — |
| Monoethylene glycol | 1500 | — | — | — |
| Sodium chloride | 100 | 32080 | 1710.9 | 32.08 |

TABLE 12-continued

| Second Model Test Solution | | | | |
|---|---|---|---|---|
| | kg | mg/kg | mol | mmol/kg |
| Magnesium chloride | 1.00 | 321 | 10.5 | 0.32 |
| Calcium chloride | 13.00 | 4170 | 117.1 | 4.17 |
| Sodium sulfate | 0.80 | 257 | 5.6 | 0.26 |
| Sodium bicarbonate | 2.40 | 770 | 28.6 | 0.77 |
| | 3117.2 | | | |

Barium chloride, sodium carbonate, and sodium hydroxide were added to the test solutions in order to precipitate the sulfate, calcium, and magnesium, respectively, according to the reactions shown below:

$$BaCl_2(aq) + Na_2SO_4(aq) \rightarrow BaSO_4(s) + 2NaCl(aq)$$

$$CaCl_2(aq) + Na_2CO_3(aq) \rightarrow CaCO_3(s) + 2NaCl(aq)$$

$$MgCl_2(aq) + 2NaOH \rightarrow Mg(OH)_2(s) + 2NaCl(aq)$$

First Model Test Solution

The addition of barium chloride to the first model test solution is shown in TABLE 13. It can be seen that sulfate is removed almost quantitatively at Ba:$SO_4$=1:1 mol:mol.

TABLE 13

| Addition of BaCl₂ to First Model Test Solution | | | | | | | |
|---|---|---|---|---|---|---|---|
| | Solution ID | | | | | | |
| | 6.1. | 6.2. | 6.3. | 6.4. | 6.5. | 6.6. | 6.7. |
| Ba:SO₄ (mol:mol) | 0.00 | 0.43 | 0.68 | 0.94 | 1.00 | 1.02 | 1.28 |
| pH | 5.92 | 5.90 | 5.89 | 5.88 | 5.88 | 5.88 | 5.87 |
| Ba Precipitated % | 0% | 99% | 99% | 98% | 96% | 95% | 78% |
| SO₄ Precipitated % | 0% | 42% | 68% | 92% | 96% | 97% | 100% |

The solution after addition of barium chloride to achieve $Ba^{2+}:SO_4^{2-}$ of 1:1 mol:mol was mixed with sodium carbonate (Solution 6.5., above). The results are shown in TABLE 14.

TABLE 14

| Addition of Na₂CO₃ to First Model Test Solution after BaCl₂ Addition | | | | | | |
|---|---|---|---|---|---|---|
| | Solution ID | | | | | |
| | 7.1. | 7.2. | 7.3. | 7.4. | 7.5. | 7.6. |
| Ba:SO₄ (mol:mol) | 1.000 | 1.000 | 1.000 | 1.000 | 1.000 | 1.000 |
| CO₃:Ca (mol:mol) | 0.000 | 0.403 | 0.806 | 0.967 | 1.000 | 1.100 |
| pH | 5.88 | 7.79 | 8.03 | 8.36 | 8.56 | 9.18 |
| Ca Precipitated | 0.0% | 40.1% | 80.2% | 95.8% | 98.3% | 99.9% |
| Ba Precipitated | 96.4% | 96.8% | 97.3% | 97.5% | 97.6% | 97.6% |
| SO₄ Precipitated | 96.4% | 96.8% | 97.3% | 97.5% | 97.6% | 97.6% |

TABLE 14 shows that calcium precipitates from solution as the sodium carbonate is added and near quantitative calcium removal is achieved at $CO_3^{2-}:Ca^{2+}=1.1:1$ mol:mol (Solution 7.6. above, 99.9% calcium precipitation). No re-dissolution of barium carbonate is predicted.

The solution after addition of barium chloride to achieve $Ba^{2+}:SO_4^{2-}$ of 1:1 mol:mol and sodium carbonate addition at $CO_3^{2-}:Ca^{2+}$ at 1.1:1 mol:mol was mixed with sodium hydroxide. The results are shown in TABLE 15.

TABLE 15

| Addition of NaOH to First Model Test Solution after BaCl₂ and Na₂CO₃ Addition | | | | | |
|---|---|---|---|---|---|
| Simulation ID | 8.1. | 8.2. | 8.3. | 8.4. | 8.5. |
| Ba:SO₄ (mol:mol) | 1.00 | 1.00 | 1.00 | 1.00 | 1.00 |
| CO₃:Ca (mol:mol) | 1.10 | 1.10 | 1.10 | 1.10 | 1.10 |
| OH:Mg (mol:mol) | 0.00 | 1.00 | 2.00 | 3.00 | 4.00 |
| pH | 9.18 | 9.50 | 9.69 | 9.87 | 10.02 |
| Mg Precipitated | 0.0% | 26.9% | 55.9% | 74.3% | 84.7% |
| Ca Precipitated | 99.9% | 99.9% | 99.9% | 99.9% | 99.9% |
| Ba Precipitated | 97.6% | 97.6% | 97.1% | 96.0% | 95.1% |
| SO₄ Precipitated | 97.6% | 97.5% | 97.1% | 96.0% | 95.1% |

TABLE 15 shows that calcium precipitation is unaffected by the addition of the sodium hydroxide solution but that barium sulfate is somewhat soluble at an elevated pH, falling from 97.6% precipitation at a pH of 9.18 to 95.1% precipitation at a pH of 10.02. Excessive addition of hydroxide should therefore be avoided to minimize re-dissolution of barium sulfates. In practice, the amounts of barium chloride, sodium carbonate, and sodium hydroxide will depend on the concentrations of sulfate, calcium, and magnesium ions present in the MEG-water stream. For example, a lower efficiency for magnesium removal may be acceptable to the operator if the concentration of magnesium ions in the MEG-water stream is also low.

Second Model Test Solution

The addition of barium chloride to the second model test solution is shown in TABLE 16. TABLE 16 shows that near-quantitative sulfate removal is achieved at $Ba^{2+}:SO_4^{2-}$ at 1.2:1 mol:mol. Barium precipitation at this $Ba^{2+}:SO_4^{2-}$ ratio falls from 100% since the barium is present in excess.

TABLE 16

| Addition of BaCl₂ to Second Model Test Solution | | | | | | |
|---|---|---|---|---|---|---|
| | Simulation ID | | | | | |
| | 9.1. | 9.2. | 9.3. | 9.4. | 9.5. | 9.6. |
| Ba:SO₄ (mol:mol) | 0.00 | 0.26 | 0.51 | 0.85 | 1.02 | 1.20 |
| pH | 6.037 | 6.036 | 6.034 | 6.032 | 6.031 | 6.031 |
| Ca Precipitated | 9.4% | 9.4% | 9.4% | 9.4% | 9.4% | 9.4% |
| Ba Precipitated % | 0% | 99% | 99% | 99% | 95% | 83% |
| SO₄ Precipitated % | 0% | 25% | 51% | 85% | 97% | 99% |
| CO₃ Precipitated % | 38.5% | 38.6% | 38.6% | 38.6% | 38.7% | 38.7% |

It should be noted that some calcium precipitation is observed under the starting conditions due to the conversion of calcium bicarbonate to calcium carbonate as per the reaction below:

$$Ca^{2+}(aq) + 2HCO_3^-(aq) \rightarrow CaCO_3(s) + CO_2(aq) + H_2O$$

TABLE 17 shows the extent of solids precipitation after the addition of sodium carbonate to the second model test solution ($Ba^{2+}:SO_4^{2-}$ at 1.2:1 mol:mol).

TABLE 17

Addition of Na₂CO₃ to Second Model Test Solution after Addition of BaCl₂

| | Sample ID | | | | | |
|---|---|---|---|---|---|---|
| | 10.1. | 10.2. | 10.3. | 10.4. | 10.5. | 10.6. |
| $Ba^{2+}:SO_4^{2-}$ (mol:mol) | 1.200 | 1.200 | 1.200 | 1.200 | 1.200 | 1.200 |
| Added $CO_3^{2-}:Ca^{2+}$ (mol:mol) | 0.000 | 0.483 | 0.725 | 0.967 | 1.047 | 1.128 |
| pH | 6.031 | 6.211 | 6.407 | 7.181 | 8.044 | 8.737 |
| Mg Precipitated | — | — | — | — | — | — |
| Ca Precipitated | 9.4% | 56.8% | 79.7% | 98.3% | 99.8% | 99.9% |
| Ba Precipitated | 82.9% | 83.0% | 83.1% | 83.1% | 82.9% | 98.1% |
| SO₄ Precipitated | 99.4% | 99.6% | 99.7% | 99.7% | 99.5% | 97.3% |
| CO₃ Precipitated | 38.7% | 78.1% | 82.3% | 81.2% | 77.3% | 72.9% |

TABLE 17 shows that near-quantitative calcium precipitation is achieved as the sodium carbonate to calcium molar ratio is elevated to 1.13 (mol:mol) while re-dissolution of sulfate occurs only to a relatively small extent. Excessive addition of sodium carbonate elevates the solution pH to a level where barium sulfate begins to re-dissolve.

TABLE 18 shows the effect of sodium hydroxide addition to the solution 10.5. shown in TABLE 17.

TABLE 18

Addition of NaOH to Second Model Test Solution after Addition of BaCl₂ and Na₂CO₃

| Sample ID | 11.1. | 11.2. | 11.3. | 11.4. | 11.5. |
|---|---|---|---|---|---|
| $Ba^{2+}:SO_4^{2-}$ (mol:mol) | 1.200 | 1.200 | 1.200 | 1.200 | 1.200 |
| Added $CO_3^{2-}:Ca^{2+}$ (mol:mol) | 1.047 | 1.047 | 1.047 | 1.047 | 1.047 |
| $OH^-:Mg^{2+}$ (mol:mol) | 0.000 | 2.380 | 3.570 | 4.760 | 7.140 |
| pH | 8.044 | 9.533 | 9.778 | 9.911 | 10.154 |
| Mg Precipitated | 0.0% | 0.0% | 31.4% | 43.1% | 76.1% |
| Ca Precipitated | 99.8% | 100.0% | 100.0% | 100.0% | 100.0% |
| Ba Precipitated | 82.9% | 99.2% | 99.4% | 99.5% | 99.6% |
| SO₄ Precipitated | 99.5% | 92.8% | 90.2% | 87.8% | 84.1% |
| CO₃ Precipitated | 77.3% | 77.4% | 78.5% | 78.6% | 78.7% |

TABLE 18 shows that magnesium precipitation requires elevated pH but that at pH of 9.5 and above re-dissolution of barium sulfate occurs, which leads to increased levels of sulfate in the resulting solution. Simultaneous quantitative precipitation (100%) of calcium, magnesium, and sulfate by the addition of carbonate, hydroxide, and barium ions cannot be achieved so the operator must consider the composition of the MEG-water stream as well as the absolute quantities and percentages of sulfate, calcium, and magnesium to be removed. Some carry-through of potentially scaling calcium, magnesium, and sulfate ions may occur, and can be managed through a combination of clean-in-place (CIP) systems and addition of appropriate scale inhibitors.

It should be noted that the barium chloride and sodium carbonate solutions should not be pre-mixed before addition to MEG-water streams since precipitation of barium carbonate may occur as shown by the reaction below:

$$BaCl_2(aq) + Na_2CO_3(aq) \rightarrow BaCO_3(s) + 2NaCl(aq)$$

However, in the presence of calcium ions and sulfate ions (i.e., in the chemical treatment tank), barium sulfate and calcium carbonate will be the preferred solid precipitants.

An advantage of the present invention is that it removes divalent cations and sulfate from MEG-water streams in order to improve the efficiency of MEG reclamation or MEG regeneration. The present invention also minimizes the formation of scale inside pipelines and process equipment, thereby improving equipment availability. Other advantages are that the present invention reduces the need for the use of clean-in-place systems and scale inhibitors and reduces the amount of time that the process equipment must be taken off-line for cleaning.

While preferred embodiments of a system and process for removing divalent ions from MEG-water streams have been described in detail, a person of ordinary skill in the art understands that certain changes can be made in the arrangement of process steps and type of components used in the system and process without departing from the scope of the following claims.

What is claimed is:

1. A process comprising:
routing a monoethylene glycol (MEG) water stream containing sulfate ions to a chemical treatment tank;
adding barium chloride to the MEG-water stream;
forming and precipitating barium sulfate in the MEG-water stream while the stream is in the chemical treatment tank; and
discharging the MEG-water stream from the chemical treatment tank.

2. A process according to claim 1 further comprising:
adding at least one of a solution of sodium carbonate, to precipitate calcium, a solution of sodium hydroxide, to precipitate magnesium, or both to the MEG-water stream in the chemical treatment tank.

3. A process according to claim 1 further comprising:
recycling a first portion of the discharged MEG-water stream to the chemical treatment tank; and
routing a second portion of the discharged MEG-water stream from the chemical treatment tank to a solids removal system.

4. A process according to claim 1 further comprising:
routing the discharged MEG-water stream from the chemical treatment tank to a solids removal system;
separating barium sulfate solids in the solids removal system; and
recycling the discharged MEG-water stream after it passes through the solids removal system to the chemical treatment tank.

5. A process according to claim 1 further comprising routing the discharged MEG-water stream after the solids removal to a filtrate tank.

* * * * *